(12) United States Patent
Suzuki et al.

(10) Patent No.: US 8,722,907 B2
(45) Date of Patent: May 13, 2014

(54) PRODUCTION PROCESS OF GLYCOLIDE

(75) Inventors: Shigeru Suzuki, Tokyo (JP); Kazuyuki Yamane, Tokyo (JP); Toshihiko Ono, Tokyo (JP); Kazuhiko Sunagawa, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 13/142,012

(22) PCT Filed: Dec. 9, 2009

(86) PCT No.: PCT/JP2009/006713
§ 371 (c)(1),
(2), (4) Date: Jun. 24, 2011

(87) PCT Pub. No.: WO2010/073512
PCT Pub. Date: Jul. 1, 2010

(65) Prior Publication Data
US 2011/0263875 A1    Oct. 27, 2011

(30) Foreign Application Priority Data

Dec. 26, 2008    (JP) ................................ 2008-333605

(51) Int. Cl.
*C07D 319/00*    (2006.01)
(52) U.S. Cl.
USPC ........................................ 549/274
(58) Field of Classification Search
USPC ........................................ 549/274
See application file for complete search history.

(56) References Cited

U.S. PATENT DOCUMENTS

| 5,830,991 | A * | 11/1998 | Shiiki et al. ............. 549/267 |
| 6,916,939 | B2 * | 7/2005 | Yamane et al. ............ 549/274 |
| 2003/0191326 | A1 | 10/2003 | Yamane et al. |
| 2004/0122240 | A1 | 6/2004 | Yamane et al. |
| 2007/0293653 | A1 | 12/2007 | Ogawa et al. |

FOREIGN PATENT DOCUMENTS

| JP | 5-287056 A | 11/1993 |
| JP | 7-138253 A | 5/1995 |
| JP | 9-328481 A | 12/1997 |
| JP | 2002-114775 A | 4/2002 |
| JP | 2004-523596 A | 8/2004 |
| JP | 2007-332113 A | 12/2007 |
| JP | 2008-001733 A | 1/2008 |
| WO | 02/14303 A1 | 2/2002 |

* cited by examiner

*Primary Examiner* — Nizal Chandrakumar
(74) *Attorney, Agent, or Firm* — Porter Wright Morris & Arthur LLP

(57) ABSTRACT

The invention provides a production process of glycolide comprising the respective steps of: Step 1 of heating a mixture containing a glycolic acid oligomer and a high boiling polar organic under normal or reduced pressure to reflux the mixture and at that time, conducting a total reflux operation in a reflux time within a range of 0.1 to 20 hours under conditions that substantially the whole amount of a distillate distilled out of a reflux system containing the mixture is refluxed into the reflux system; Step 2 of heating the mixture after the total reflux operation or a mixture obtained by adding the high boiling polar organic solvent to a glycolic acid oligomer component recovered from the mixture after the total reflux operation to conduct depolymerization; and Step 3 of collecting glycolide from a co-distillate.

14 Claims, 2 Drawing Sheets

PRODUCTION PROCESS OF GLYCOLIDE

TECHNICAL FIELD

The present invention relates to a process for producing glycolide having a high purity by depolymerization of a glycolic acid oligomer in a solution phase.

BACKGROUND ART

Polyglycolic acid is a resin material excellent in biodegradability, gas barrier properties, strength, etc., and is used in a wide variety of technical fields as medical polymeric materials for surgical sutures, artificial skins, etc.; packaging materials for bottles, films, etc.; and resin materials for various industrial products such as injection-molded products, fibers, deposition films and fishing lines.

In order to use the polyglycolic acid as resin materials for various technical fields, the polyglycolic acid is required to have a polymerization degree suitable for the respective uses. In addition, reduction in production cost is an important problem for developing new uses of the polyglycolic acid. In order to solve these requirement and problem, the mass production, high purification and reduction in cost of glycolide used as a monomer are strongly required.

The polyglycolic acid is a polymer having a repeating unit of a structure formed by dehydration polycondensation of glycolic acid. However, the process by the dehydration polycondensation of glycolic acid only provides low-polymerization degree polyglycolic acid having a weight-average molecular weight of 20,000 or lower. The low-polymerization degree polyglycolic acid is generally called a glycolic acid oligomer and insufficient in strength, melt processability, gas barrier properties, etc. The low-polymerization degree polyglycolic acid is too fast in degradation rate under a natural environment and in vivo and cannot satisfy the requirement of durability when it is applied to many uses.

According to the process by the dehydration polycondensation of glycolic acid, it is difficult to control the polymerization degree of the resulting polyglycolic acid. In particular, it is extremely difficult at the present state of the art to synthesize high-polymerization degree polyglycolic acid. It is also difficult to synthesize high-polymerization degree polyglycolic acid even when an alkyl ester of glycolic acid is used as a monomer to conduct dealcoholization-polycondensation.

According to a process of subjecting glycolide to ring-opening polymerization, it is easy to control of the polymerization degree of the resulting polyglycolic acid, and high-polymerization degree polyglycolic acid can be synthesized. The glycolide is a cyclic ester compound having a cyclic dimeric structure formed by eliminating two molecules of water from two molecules of glycolic acid. However, glycolide cannot be synthesized even by a dehydration reaction of glycolic acid, but low-polymerization degree polyglycolic acid (glycolic acid oligomer) is only obtained.

As a production process of glycolide, a process of depolymerizing a glycolic acid oligomer is representative. Specifically, glycolic acid is polycondensed according to the following reaction formula 4:

[Chem. 1]

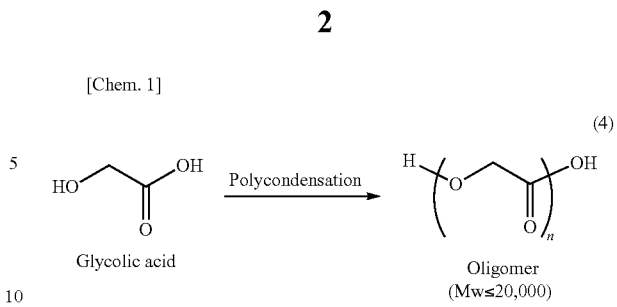

(4)

to synthesize a glycolic acid oligomer having a low polymerization degree. The glycolic acid oligomer is then depolymerized according to the following reaction formula 5:

[Chem. 2]

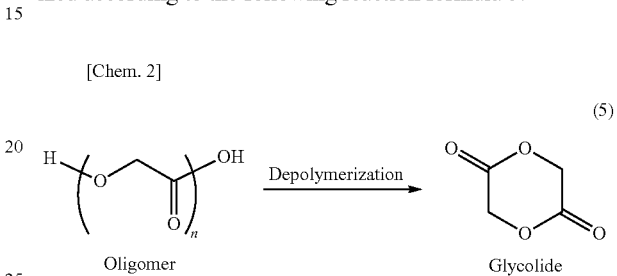

(5)

to synthesize glycolide. When the glycolide is subjected to ring-opening polymerization, polyglycolic acid can be produced according to the following reaction formula 6:

[Chem. 3]

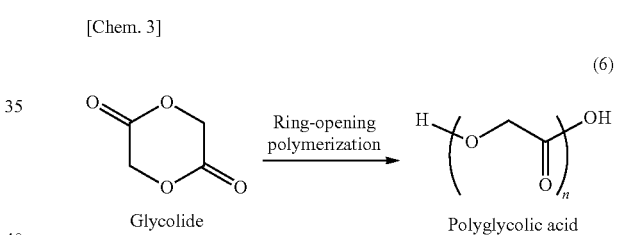

(6)

According to the ring-opening polymerization of glycolide, high-polymerization degree polyglycolic acid can be synthesized, and the polymerization degree thereof can be easily controlled.

Various proposals have been made on a process for synthesizing glycolide by depolymerization of a glycolic acid oligomer. Among these, a solution phase depolymerization process has been proposed as a process suitable for mass production of glycolide. The solution phase depolymerization process is a process, in which a mixture containing a glycolic acid oligomer and a high boiling polar organic solvent is heated to form a solution phase of the glycolic acid oligomer, and the heating is continued in that state to conduct depolymerization. When there is need to raise the solubility of the glycolic acid oligomer in the high boiling polar organic solvent, a solubilizing agent is contained in the mixture.

Japanese Patent Application Laid-Open No. 9-328481 (Patent Literature 1) has proposed a production process of a cyclic dimeric ester, in which an α-hydroxycarboxylic acid oligomer such as a glycolic acid oligomer is heated in a high boiling polar organic solvent to dissolve the oligomer, the heating is continued in that state to conduct depolymerization, a cyclic dimeric ester formed is distilled out together with the high boiling polar organic solvent, and the cyclic dimeric ester (for example, glycolide) is recovered from the distillate.

Domestic Republication of WO 02/014303 (Patent Literature 2) has proposed a production process of a cyclic ester, in which a mixture containing an aliphatic polyester such as low-molecular weight polyglycolic acid and a specific polyalkylene glycol ether is heated to a temperature at which depolymerization of the aliphatic polyester takes place to form a homogeneous solution phase, the aliphatic polyester is depolymerized in this state, a cyclic ester formed by the depolymerization is distilled out together with the polyalkylene glycol ether, and the cyclic ester (for example, glycolide) is recovered from the distillate.

Japanese Patent Application Laid-Open No. 2004-523596 (Patent Literature 3) discloses a production process of glycolide, in which a depolymerization reaction is continuously conducted while continuously or intermittently pouring a glycolic acid oligomer or a mixture of a glycolic acid oligomer and a high boiling polar organic solvent into a depolymerization reaction system containing a glycolic acid oligomer and a high boiling polar organic solvent.

According to the processed disclosed in Patent Literatures 1 to 3, the depolymerization reaction can be stably performed in addition to the fact that glycolide can be mass-produced. According to the process disclosed in Patent Literature 3 in particular, lowering of the rate of production of glycolide and the formation of tar, which are caused by impurities accumulated in the depolymerization reaction system, can be inhibited even when the depolymerization reaction is continuously conducted in the same reaction vessel.

In the processes disclosed in Patent Literatures 1 to 3, a high boiling non-basic compound is used as a solubilizing agent, the solubility of the glycolic acid oligomer in the high boiling polar organic solvent can be raised, and moreover the rate of production and yield of glycolide can be improved.

When a depolymerization reaction is continuously performed in the same apparatus while continuously or intermittently pouring a glycolic acid oligomer into the depolymerization reaction system containing a glycolic acid oligomer and a high boiling polar organic solvent, the operation can be continuously conducted over a relatively long period of time. However, it has been found that when the operation is continuously conducted for several months or longer by this process, the blocking of a line through a piping, a heat exchanger, etc. is caused.

In the depolymerization reaction, the mixture containing the glycolic acid oligomer and the high boiling polar organic solvent in the reaction vessel is heated to conduct depolymerization, and glycolide formed is distilled out together with the high boiling polar organic solvent. The co-distillate is guided to the outside of the depolymerization reaction system via the line through the piping, heat exchanger, etc. The depolymerization reaction is generally performed under reduced pressure. The co-distillate is cooled by the heat exchanger and liquefied. Glycolide is recovered from the liquid co-distillate. The high boiling polar organic solvent contained in the co-distillate is refluxed into the depolymerization reaction system. A glycolic acid oligomer is newly added into the depolymerization reaction system for supplementing the glycolic acid oligomer consumed by the depolymerization.

According to this process, the operation can be continuously conducted for a relatively long period of time. However, it has been found that when the continuously operating period is extended to several months or longer, impurities contained in the depolymerization reaction system act as a polymerization initiator to oligomerize a part of glycolide formed to block the line. When the line is blocked, the predetermined degree of reduced pressure cannot be retained, and soon the continuation of the operation becomes impossible. Therefore, the operation must be stopped after a certain period of time has elapsed to clean the whole apparatus including the line through the piping, heat exchanger, etc. It takes about 2 to 3 weeks for the cleaning though it varies according to the scale and structure of the apparatus. Frequent stopping of the operation and the cleaning treatment directly connect with increase in production cost.

The conventional glycolide obtained by the depolymerization of the glycolic acid oligomer is insufficient in purity and called crude glycolide. Glycolide used as a monomer for ring-opening polymerization is required to have a high purity of 99.9% or higher. Therefore, the crude glycolide obtained by the depolymerization is highly purified by purification treatments such as recrystallization and washing. When the purity of the crude glycolide is low, blocking of the line may be caused in some cases in addition to the fact that purification cost cannot be reduced.

The main cause of the line blocking in the depolymerization reaction is presumed to be attributable to the fact that impurities contained in a distillate distilled out of the depolymerization reaction system act as a polymerization initiator to oligomerize glycolide formed by the depolymerization and distilled off in the course of the line to block the line, and this oligomer attaches to the surfaces of respective parts of the apparatus. In fact, the crude glycolide obtained by the depolymerization contains various impurities.

When the crude glycolide obtained by the depolymerization is analyzed, water and various organic acids are detected as principal impurities. Glycolic acid, a linear glycolic acid dimer, a linear glycolic acid trimer, etc. are detected as the organic acids. Such impurities are presumed to include those contained in the glycolic acid oligomer and formed during the depolymerization reaction of the glycolic acid oligomer.

These impurities are presumed to not only react with glycolide formed even in the depolymerization reaction system containing the glycolic acid oligomer and the high boiling polar organic solvent to increase the amount of the impurities, but also cause ring-opening polymerization of the glycolide in the course of the line to form the cause of the line blocking during the continuous operation over a long period of time.

CITATION LIST

Patent Literature

Patent Literature 1: Japanese Patent Application Laid-Open No. 9-328481
Patent Literature 2: Domestic Republication of WO 02/014303
Patent Literature 3: Japanese Patent Application Laid-Open No. 2004-523596 through PCT route

SUMMARY OF INVENTION

Technical Problem

It is an object of the present invention to provide a novel production process of glycolide according to a process of depolymerizing a glycolic acid oligomer in a solution phase, by which glycolide having a high purity can be obtained.

When a depolymerization reaction of a glycolic acid oligomer is conducted by a solution phase depolymerization process, the purity of glycolide obtained from a co-distillate at an initial stage is particularly low. The reason for it is presumed to be attributable to the fact that impurities having a low boiling point are liable to be distilled off at the initial stage. When the depolymerization reaction is continued, the purity of glycolide shows a tendency to improve. However, when the glycolic acid oligomer is continuously or intermittently added into the depolymerization reaction system to continuously conduct the operation, the purity of glycolide obtained just after the addition is lowered again.

In order to inhibit impurities contained in a distillate from acting as an polymerization initiator to oligomerize glycolide in a production line, it is necessary that a glycolic acid oligomer or a mixture containing the glycolic acid oligomer and a high boiling polar organic solvent, which is fed to a depolymerization reaction, is one hard to distill out impurities.

As methods for reducing the amount of impurities, a method of highly purifying glycolic acid as a raw material, a method of purifying the glycolic acid oligomer and a method of combining these methods are considered. However, all the methods are high in cost.

The present inventors have paid attention to the fact that the formation of glycolide having a high purity has an extremely important technical meaning for inhibiting line blocking to realize a stable continuous operation of a depolymerization reaction. If glycolide having a high purity can be obtained by the depolymerization reaction, it can be inhibited that the glycolide distilled out of the depolymerization reaction system is oligomerized by the influence of impurities in the course of the line, and the oligomer attaches to the surface of the line through the piping, heat exchanger, etc. to block the line. If the glycolide having a high purity can be obtained by the depolymerization, purification cost can be reduced, and moreover the line blocking in a purification step can also be prevented.

The present inventors have carried out an extensive investigation with a view toward solving the above problems. As a result, it has been found that glycolide having a high purity of at least 99.0% is obtained by adopting, in a production process of glycolide comprising a step of heating a mixture containing a glycolic acid oligomer and a high boiling polar organic solvent, thereby depolymerizing the glycolic acid oligomer in a solution phase, a process of subjecting the mixture to a total reflux operation and then depolymerizing the glycolic acid oligomer.

It is an unexpected surprising result viewed from technical common sense that the total reflux operation is conducted, thereby obtaining high-purity glycolide in the subsequent depolymerization reaction step. The fact that the high-purity glycolide is obtained means that the amount of impurities contained in a distillate distilled out of the depolymerization reaction system is reduced. When the amount of impurities in the distillate passed through the line is reduced, the blocking of the line due to the oligomerization of glycolide caused by the impurities is inhibited. When the high-purity glycolide is obtained by the depolymerization, a burden on a purification step is relieved, and blocking of a purification line is also inhibited.

The present invention has been led to completion on the basis of these findings.

Solution to Problem

According to the present invention, there is provided a production process of glycolide comprising a step of heating a mixture containing a glycolic acid oligomer and a high boiling polar organic solvent, thereby depolymerizing the glycolic acid oligomer in a solution phase, the process comprising the respective steps of:

(1) Step 1 of heating the mixture containing the glycolic acid oligomer and the high boiling polar organic solvent having a boiling point within a range of 230 to 450° C. under normal or reduced pressure to reflux the mixture and at that time, conducting a total reflux operation in a reflux time within a range of 0.1 to 20 hours under conditions that substantially the whole amount of a distillate distilled out of a reflux system containing the mixture is refluxed into the reflux system;

(2) Step 2 of heating the mixture after the total reflux operation or a mixture obtained by adding the high boiling polar organic solvent to a glycolic acid oligomer component recovered from the mixture after the total reflux operation under normal or reduced pressure to a temperature at which the glycolic acid oligomer is depolymerized to depolymerize the glycolic acid oligomer in a solution phase, and moreover co-distilling glycolide formed by the depolymerization out of the depolymerization reaction system containing the mixture together with the high boiling polar organic solvent into the outside of the depolymerization reaction system; and (3) Step 3 of collecting the glycolide from the co-distillate.

Advantageous Effects of Invention

According to the present invention, high-purity glycolide can be produced by the depolymerization of a glycolic acid oligomer in a solution phase. When the production process according to the present invention is applied to a depolymerizing step of glycolide by a continuous operation, the blocking of the line can be inhibited, so that long-term operativity (long-run operativity) can be markedly improved. The high-purity glycolide also contributes to reduction in a burden on the subsequent purification step and inhibition of line blocking. As a result, the production process according to the present invention permits not only reducing the production cost of the glycolide, but also contributing to reduction in the production cost of polyglycolic acid.

DESCRIPTION OF EMBODIMENTS

1. Glycolic Acid Oligomer

Figure 1:
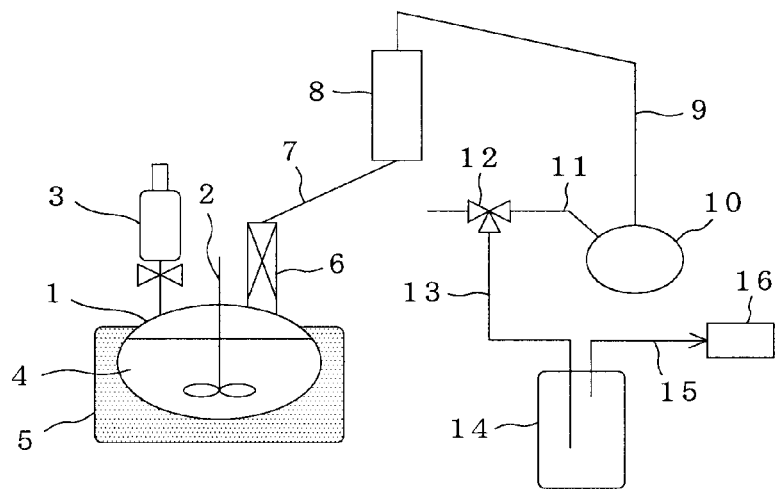
FIG. 1 is an explanatory view illustrating an exemplary apparatus for conducting total reflux.

A glycolic acid oligomer is low-polymerization degree (low-molecular weight) polyglycolic acid having a weight-average molecular weight (Mw) of 20,000 or lower, often 10,000 or lower. The glycolic acid oligomer can be synthesized by polycondensation of glycolic acid. The glycolic acid may be in the form of an ester (for example, lower alkyl ester) or salt (for example, sodium salt) thereof.

The glycolic acid is heated to a temperature of generally 100 to 250° C., preferably 140 to 230° C. in the presence of an optional condensation catalyst or transesterification catalyst to conduct a polycondensation reaction until low-molecular weight compounds such as water and alcohol have substantially ceased to be distilled out. After completion of the polycondensation reaction, the glycolic acid oligomer formed may be used as a raw material as it is. The glycolic acid oligomer obtained by the synthesis may be washed with a non-solvent such as benzene or toluene to remove an unreacted material, low polymers and the catalyst before its use. The glycolic acid oligomer preferably has a melting point (Tm) of generally 140° C. or higher, preferably 160° C. or higher, more preferably 180° C. or higher from the viewpoint of yield of the glycolide formed by the depolymerization reaction. Here, the melting point is a temperature detected as an endothermic peak temperature at the time the oligomer is heated at a rate of 10° C./min in an inert gas atmosphere by means of a differential scanning calorimeter (DSC). The upper limit of the melting point is about 220° C.

2. High Boiling Polar Organic Solvent

A high boiling polar organic solvent is used as a medium in the total reflux operation step and depolymerization reaction step. In the present invention, a high boiling polar organic solvent having a boiling point within a range of 230 to 450° C. is used. In order to conduct the depolymerization of the glycolic acid oligomer according to the solution phase depolymerization process, it is necessary for forming a solution phase of the glycolic acid oligomer to use a high boiling polar organic solvent as a solvent. The high boiling polar organic solvent is used as the solvent for the depolymerization reaction, and fulfills the role of being co-distilled out together with the glycolide formed to accompany the glycolide to the outside of the depolymerization reaction system. The high boiling polar organic solvent is co-distilled out together with the glycolide, whereby the glycolide can be prevented from attaching to an inner wall surface of the line.

If the boiling point of the high boiling polar organic solvent is too low, the temperature of the depolymerization reaction cannot be set high, and so the rate of formation of the glycolide is lowered. If the boiling point of the high boiling polar organic solvent is too high, such a high boiling polar organic solvent is hard to be distilled out upon the depolymerization reaction, and so it is hard to co-distill out it together with the glycolide formed by the depolymerization reaction. The boiling point of the high boiling polar organic solvent is within a range of preferably 235 to 450° C., more preferably 255 to 430° C., most preferably 280 to 420° C. The boiling point of the high boiling polar organic solvent is a value under normal pressure. When the boiling point is measured under reduced pressure, the measured value is converted to a value under normal pressure.

The molecular weight of the high boiling polar organic solvent is within a range of preferably 150 to 450, more preferably 180 to 420, still more preferably 200 to 400. A high boiling polar organic solvent having a too low or high molecular weight is not preferred because it is difficult to co-distill out it together with the glycolide.

Even in the total reflux operation step of the present invention, the high boiling polar organic solvent is used as a medium for smoothly performing the total reflux operation to efficiently achieve the effect to reduce the amount of impurities by the total reflux operation and moreover smoothly performing the depolymerization reaction in the subsequent depolymerization reaction step.

Examples of the high boiling polar organic solvent include aromatic dicarboxylic acid diesters, aromatic carboxylic acid esters, aliphatic dicarboxylic acid diesters, polyalkylene glycol diethers, aromatic dicarboxylic acid dialkoxyalkyl esters, aliphatic dicarboxylic acid dialkoxyalkyl esters, polyalkylene glycol diesters and aromatic phosphoric acid esters.

Among these high boiling polar organic solvents, aromatic dicarboxylic acid diesters, aromatic carboxylic acid esters, aliphatic dicarboxylic acid diesters and polyalkylene glycol diethers are preferred, and polyalkylene glycol diethers are more preferred in that they are hard to cause deterioration by heat.

Examples of the aromatic dicarboxylic acid diesters include phthalic acid esters such as dibutyl phthalate, dioctyl phthalate, dibenzyl phthalate and benzylbutyl phthalate.

Examples of the aromatic carboxylic acid esters include benzoic acid esters such as benzyl benzoate. Examples of the aliphatic dicarboxylic acid diesters include adipic acid esters such as dioctyl adipate; and sebacic acid esters such as dibutyl sebacate.

As the polyalkylene glycol diethers, are preferred polyalkylene glycol diethers represented by the following formula 1:

[Chem. 4]

(1)

(in the formula, $R^1$ is a methylene group, or a linear or branched alkylene group having 2 to 8 carbon atoms, $X^1$ is a hydrocarbon group, Y is an alkyl group having 2 to 20 carbon atoms or an aryl group, and p is an integer of 1 or greater, with the proviso that when p is 2 or greater, plural $R^1$ groups may be the same or different from each other.) and having a molecular weight of 150 to 450.

Specific examples of the polyalkylene glycol diethers include polyethylene glycol dialkyl ethers such as diethylene glycol dibutyl ether, diethylene glycol dihexyl ether, diethylene glycol dioctyl ether, diethylene glycol butyl 2-chlorophenyl ether, triethylene glycol diethyl ether, triethylene glycol dipropyl ether, triethylene glycol dibutyl ether, triethylene glycol dihexyl ether, triethylene glycol dioctyl ether, triethylene glycol butyl octyl ether, triethylene glycol butyl decyl ether, tetraethylene glycol diethyl ether, tetraethylene glycol dipropyl ether, tetraethylene glycol dibutyl ether, tetraethylene glycol dihexyl ether, tetraethylene glycol dioctyl ether, diethylene glycol butyl hexyl ether, diethylene glycol butyl octyl ether, diethylene glycol hexyl octyl ether, triethylene glycol butyl hexyl ether, triethylene glycol hexyl octyl ether, tetraethylene glycol butyl hexyl ether, tetraethylene glycol butyl octyl ether and tetraethylene glycol hexyl octyl ether; polyalkylene glycol dialkyl ethers such as polypropylene glycol dialkyl ethers and polybutylene glycol dialkyl ethers, which contain a propyleneoxy or butyleneoxy group in stead of the ethyleneoxy group in the polyethylene glycol dialkyl ethers described above; polyethylene glycol alkyl aryl ethers such as diethylene glycol butyl phenyl ether, diethylene glycol hexyl phenyl ether, diethylene glycol octyl phenyl ether, triethylene glycol butyl phenyl ether, triethylene glycol hexyl phenyl ether, triethylene glycol octyl phenyl ether, tetraethylene glycol butyl phenyl ether, tetraethylene glycol hexyl phenyl ether and tetraethylene glycol octyl phenyl ether, and compounds which substitute any of alkyl groups, alkoxyl groups, halogen atoms, etc. for at least one hydrogen atom of the phenyl group in these compounds; polyalkylene glycol alkyl aryl ethers such as polypropylene glycol alkyl aryl ethers and polybutylene glycol alkyl aryl ethers, which contain a propyleneoxy or butyleneoxy group in stead of the ethyleneoxy group in the polyethylene glycol alkyl aryl ethers described above; polyethylene glycol diaryl ethers such as diethylene glycol diphenyl ether, triethylene glycol diphenyl ether, tetraethylene glycol diphenyl ether, and compounds which substitute any of alkyl groups, alkoxyl groups, halogen atoms, etc. for at least one phenyl groups in these compounds; and polyalkylene glycol diaryl ethers such as polypropylene glycol diaryl ethers and polybutylene glycol diaryl ethers, which contain a propyleneoxy or butyleneoxy group in stead of the ethyleneoxy group in the polyethylene glycol diaryl ethers described above.

As the polyalkylene glycol diethers, polyalkylene glycol dialkyl ethers are preferred in that they are easy to be synthesized and hard to cause deterioration by heat, and diethylene glycol dialkyl ethers, triethylene glycol dialkyl ethers and tetraethylene glycol dialkyl ethers are more preferred.

The solubility of glycolide in the polyalkylene glycol diether at 25° C. is preferably within a range of 0.1 to 10%. The solubility of glycolide is expressed as a percentage of the mass (g) of the glycolide to the volume (ml) of the polyalkylene glycol diether when the glycolide is dissolved to the saturation in the polyalkylene glycol diether at 25° C.

If this solubility is too low, the glycolide distilled out together with the polyalkylene glycol diether deposits, and blocking of a recovery line, or the like is easy to occur, and so such a solvent is not preferred. If the solubility is too high, recovery of the glycolide from the co-distillate obtained by depolymerization reaction requires to isolate the glycolide by, for example, cooling the co-distillate to a temperature of 0° C. or lower and/or adding a non-solvent to the co-distillate.

Preferable specific examples of the polyalkylene glycol diether include tetraethylene glycol dibutyl ether (boiling point=340° C., molecular weight=306, solubility of glycolide=4.6%), triethylene glycol butyl octyl ether (boiling point=350° C., molecular weight=350, solubility of glycolide=2.0%), triethylene glycol butyl decyl ether (boiling point=400° C., molecular weight=400, solubility of glycolide=1.3%), diethylene glycol dibutyl ether (boiling point=256° C., molecular weight=218, solubility of glycolide=1.8%) and diethylene glycol butyl 2-chlorophenyl ether (boiling point=345° C., molecular weight=273, solubility of glycolide=1.8%). Among these, tetraethylene glycol dibutyl ether and triethylene glycol butyl octyl ether are more preferred from the viewpoint of ease of synthesis, resistance to thermal deterioration, depolymerization reaction property and glycolide-recovering ability.

The high boiling polar organic solvent is used in a proportion of generally 0.3 to 50 times by mass, preferably 0.5 to 20 times by mass as much as the glycolic acid oligomer. If the proportion of the high boiling polar organic solvent is too low, it is difficult to conduct the total reflux operation, and a proportion of the solution phase of the glycolic acid oligomer in the mixture containing the glycolic acid oligomer and the high boiling polar organic solvent is lowered under temperature conditions for depolymerization to lower the depolymerization reactivity of the glycolic acid oligomer. If the proportion of the high boiling polar organic solvent is too high, a thermal efficiency in the total reflux operation and depolymerization reaction is lowered, and productivity of glycolide by the depolymerization reaction is also lowered.

3. Solubilizing Agent

In the production process according to the present invention, the high boiling polar organic solvent may be used singly in the total reflux operation and depolymerization reaction steps. However, a solubilizing agent is preferably used in combination. It has been found that when the solubilizing agent is used in the total reflux operation step, the purity of the glycolide obtained by the depolymerization is more improved. When the solubilizing agent is used in the depolymerization reaction step, the depolymerization of the glycolic acid oligomer in the solution phase state is caused to efficiently proceed.

The solubilizing agent used in the present invention is preferably a compound satisfying at least one of the following requirements:

(1) It should be a non-basic compound. A basic compound such as an amine, pyridine or quinoline is not preferred because it may possibly react with the aliphatic polyester and/or the cyclic ester formed.

(2) It should be a compound miscible with or soluble in the high boiling polar organic solvent such as a polyalkylene glycol diether. It may be liquid or solid at normal temperature so far as it is a compound miscible with or soluble in the high boiling polar organic solvent.

(3) It should be a compound having a boiling point of at least 180° C., preferably at least 200° C., more preferably at least 230° C., particularly preferably at least 250° C.

(4) It should be a compound having a functional group such as, for example, an OH, COOH or CONH group.

(5) It should have higher affinity for the glycolic acid oligomer rather than for the high boiling polar organic solvent. The affinity of the solubilizing agent for the glycolic acid oligomer can be confirmed by heating a mixture of the glycolic acid oligomer and the high boiling polar organic solvent to a temperature 230° C. or higher to form a homogeneous solution phase, further adding the glycolic acid oligomer thereto to increase the concentration of the glycolic acid oligomer until the mixture does not form a homogeneous solution phase any longer, and adding the solubilizing agent thereto to visually observe whether a homogeneous solution phase is formed again or not.

A compound having a boiling point higher than that of the high boiling polar organic solvent used in the depolymerization reaction is preferably used as the solubilizing agent because such a compound is not distilled out or extremely slightly distilled together with glycolide and the high boiling polar organic solvent when the glycolide is distilled out. In most cases, a good result can be obtained by using a compound having a boiling point of 450° C. or higher as the solubilizing agent. Alcohols and the likes may be preferably used as the solubilizing agent even when they are compounds having a boiling point lower than that of the high boiling polar organic solvent used as the solvent for the depolymerization.

The solubilizing agent is preferably at least one non-basic organic compound selected from the group consisting of monohydric alcohols, polyhydric alcohols, phenols, monovalent aliphatic carboxylic acids, polyvalent aliphatic carboxylic acids, aliphatic amides, aliphatic imides, polyalkylene glycol diethers having a molecular weight higher than 450 and sulfonic acids, said compounds each having a boiling point of 180° C. or higher.

Among these non-basic compounds, monohydric alcohols and polyhydric alcohol are particularly effective as the solubilizing agent. A monohydric or polyhydric alcohol having a boiling point of at least 180° C., preferably at least 200° C., more preferably at least 230° C., particularly preferably at least 250° C. may be used as the monohydric or polyhydric alcohol.

Examples of the monohydric or polyhydric alcohols include aliphatic alcohols such as decanol, tridecanol, decanediol, ethylene glycol, propylene glycol, and glycerol; aromatic alcohols such as cresols, chlorophenols and naphthyl alcohol; polyalkylene glycols; and polyalkylene glycol monoethers.

As the monohydric alcohols, are preferred polyalkylene glycol monoethers represented by the following formula 2:

[Chem. 5]

$$HO{-}(R^2{-}O){-}_q X^2 \qquad (2)$$

(in the formula, $R^2$ is a methylene group, or a linear or branched alkylene group having 2 to 8 carbon atoms, $X^2$ is a hydrocarbon group, and q is an integer of 1 or greater, with the proviso that when q is 2 or greater, plural $R^2$ groups may be the same or different from each other.) and having a boiling point of 250° C. or higher.

Specific examples of the polyalkylene glycol monoether include polyethylene glycol monoethers such as polyethylene glycol monomethyl ethers, polyethylene glycol monoethyl ethers, polyethylene glycol monopropyl ethers, polyethylene glycol monobutyl ethers, polyethylene glycol monohexyl ethers, polyethylene glycol monooctyl ethers, polyethylene glycol monodecyl ethers and polyethylene glycol monolauryl ethers; and polyalkylene glycol monoethers, such as polypropylene glycol monoethers and polybutylene glycol monoethers, which contain a propyleneoxy or butyleneoxy group instead of the ethyleneoxy group in the polyethylene glycol monoethers described above.

The polyethylene glycol monoethers preferably have an alkyl group having 1 to 18 carbon atoms and more preferably an alkyl group having 6 to 18 carbon atoms within the ether group thereof. These compounds may be used either singly or in any combination thereof. Among the polyalkylene glycol monoethers, polyethylene glycol monoalkyl ethers such as triethylene glycol monooctyl ether are preferred.

When a polyalkylene glycol monoether is used as the solubilizing agent, this compound is scarcely distilled out due to its high boiling point. In addition, since the polyalkylene glycol monoether dissolves the glycolic acid oligomer to a great extent, the depolymerization reaction of the glycolic acid oligomer is caused to rapidly proceed when this compound is used as the solubilizing agent. When the polyalkylene glycol monoether is used as the solubilizing agent, an effect to clean a tank wall (an inner wall of a reaction vessel) becomes particularly excellent.

As the polyhydric alcohols, are preferred polyalkylene glycols represented by the following formula 3:

[Chem. 6]

(3)

(in the formula, $R^3$ is a methylene group, or a linear or branched alkylene group having 2 to 8 carbon atoms, and r is an integer of 1 or greater, with the proviso that when r is 2 or greater, plural $R^3$ groups may be the same or different from each other.) and having a boiling point of 250° C. or higher.

Specific examples of the polyalkylene glycol include polyethylene glycol, polypropylene glycol and polybutylene glycol. These compounds may be used either singly or in any combination thereof.

A polyalkylene glycol diether, which has higher affinity for the glycolic acid oligomer than for the high boiling polar organic solvent used in the total reflux operation and depolymerization reaction steps, a high molecular weight and a high boiling point, may be used as the solubilizing agent. Specific examples of the polyalkylene glycol diether suitable for use as the solubilizing agent include polyethylene glycol dimethyl ether #500 (average molecular weight: 500) and polyethylene glycol dimethyl ether #2000 (average molecular weight: 2000). The polyalkylene glycol diether used as the solubilizing agent has a molecular weight of 450 or higher. If this molecular weight is low, in some cases, such a polyalkylene glycol diether may be distilled out together with the glycolide during the depolymerization reaction, and its function as the solubilizing agent retaining the solubility of the glycolic acid oligomer in the depolymerization reaction system may not be sufficiently fulfilled.

Although the action of the solubilizing agent is not yet completely clarified, it is considered to be attributable to 1) an effect that it reacts with a terminal of the glycolic acid oligomer to change the glycolic acid oligomer to a more soluble matter, 2) an effect that it acts on the molecular chain of the glycolic acid oligomer at an intermediate site thereof to cleave the molecular chain thereof, thereby modifying the molecular weight thereof to change the glycolic acid oligomer to a more soluble matter, 3) an effect that the polarity of the whole solvent system is changed to enhance hydrophilicity, thereby enhancing the solubility of the glycolic acid oligomer in the solvent, 4) an effect to disperse and emulsify the glycolic acid oligomer, 5) an effect that it bonds to one terminal of the glycolic acid oligomer to increase depolymerization reaction points, 6) an effect that it acts on an intermediate site of the glycolic acid oligomer to cleave the molecular chain thereof and moreover bonds to the terminals of the molecular chains cleaved to increase depolymerization reaction points, and 7) the combined effect thereof.

When the solubilizing agent is used, it is used in a proportion of generally 0.1 to 500 parts by mass, preferably 1 to 300 parts by mass per 100 parts by mass of the glycolic acid oligomer. If the proportion of the solubilizing agent used is too low, the effect to improve the solubilization by the solubilizing agent is not sufficiently achieved. If the proportion of the solubilizing agent used is too high, recovery of the solubilizing agent is costly and uneconomical.

4. Total Reflux Operation Step

In the present invention, the mixture containing the glycolic acid oligomer and the high boiling polar organic solvent is heated to conduct the depolymerization of the glycolic acid oligomer according to the solution phase depolymerization process. However, the total reflux operation of the mixture is conducted prior to this depolymerization reaction step.

In the total reflux operation step, the mixture containing the glycolic acid oligomer and the high boiling polar organic solvent having a boiling point within a range of 230 to 450° C. is heated under normal or reduced pressure to reflux the mixture and at that time, a total reflux operation is conducted in a reflux time within a range of 0.1 to 20 hours under conditions that substantially the whole amount of a distillate distilled out of a reflux system containing the mixture is refluxed into the reflux system.

The high boiling polar organic solvent is used in a proportion of generally 0.3 to 50 times by mass, preferably 0.5 to 20 times by mass as much as the glycolic acid oligomer. If the proportion of the high boiling polar organic solvent is too low, it is difficult to conduct the total reflux operation. If the proportion of the high boiling polar organic solvent is too high, a thermal efficiency in the total reflux operation is lowered.

The mixture used in the total reflux operation is preferably a mixture further containing, as a solubilizing agent, at least one non-basic organic compound selected from the group consisting of monohydric alcohols, polyhydric alcohols, phenols, monovalent aliphatic carboxylic acids, polyvalent aliphatic carboxylic acids, aliphatic amides, aliphatic imides, polyalkylene glycol diethers having a molecular weight higher than 450 and sulfonic acids, said compounds each having a boiling point of 180° C. or higher, in addition to the glycolic acid oligomer and the high boiling polar organic solvent.

By using the solubilizing agent, higher-purity glycolide can be obtained in the depolymerization reaction step after the total reflux operation. When the solubilizing agent is used in the total reflux operation step, the solubilizing agent is used in a proportion of generally 0.1 to 500 parts by mass, preferably 1 to 300 parts by mass per 100 parts by mass of the glycolic acid oligomer.

When the solubilizing agent is used in the total reflux operation step, the molar ratio (glycolic acid oligomer/solubilizing agent) of the glycolic acid oligomer to the solubilizing agent is controlled within a range of preferably 1 to 99, more preferably 3 to 70, still more preferably 5 to 50, whereby higher-purity glycolide can be obtained.

The total reflux operation may be conducted under normal or reduced pressure. However, the total reflux operation is preferably conducted under reduced pressure for smoothly conducting the operation because the high boiling polar organic solvent is used. The degree of reduced pressure is within a range of preferably 1 to 30 kPa, more preferably 1.5 to 20 kPa, still more preferably 2 to 10 kPa, particularly preferably 2.5 to 8 kPa.

The total reflux operation can be performed by means of a reactor (reaction vessel) equipped with a reflux condenser tube (reflux condenser column). A stirring means such as a stirring device equipped with a stirring blade is arranged in the interior of the reaction vessel, a heating means such as a heater is arranged in the exterior of the reaction vessel. The glycolic acid oligomer, the high boiling polar organic solvent and optionally the solubilizing agent are poured into the reaction vessel, and a mixture containing these is heated with stirring.

FIG. 1 schematically illustrates an exemplary reflux apparatus. A stirring device 2 equipped with a stirring blade is arranged in a reaction vessel 1, and the glycolic acid oligomer, the high boiling polar organic solvent and optionally the solubilizing agent are poured into the reaction vessel 1 from a raw material input port 3 to form a reflux system comprising a mixture 4. A heating means 5 such as a mantle heater is arranged in the exterior of the reaction vessel 1 to heat the mixture 4, thereby dissolving the glycolic acid oligomer to form a solution phase.

When the heating is continued, a distillate containing the high boiling polar organic solvent is distilled out of the reflux system and reaches a reflux condenser tube 8 through a piping 7 from a distillation column 6, and the distillate is cooled therein and refluxed into the original reflux system. Low-boiling matter passed through the reflux condenser tube 8 is trapped in a first cooling trap (for example, an ice bath trap) 10 through a piping 9. In order to conduct the total reflux operation under reduced pressure, a piping 15 is connected to a vacuum device (vacuum pump) 16. The first cooling trap 10 is connected to a second cooling trap 14 (for example, a dry ice trap) through a piping 11, a valve 12 and a piping 13 and is so constructed that low-boiling matter not trapped in the first cooling trap is trapped in the second cooling trap. The distillation column 6 fulfills the role of controlling the temperature of the distillate in such a manner that the distillate smoothly reaches the reflux condenser tube 8 from the piping 7.

The heating temperature is set to a temperature at which the high boiling polar organic solvent is distilled out. The heating temperature varies according to the kind of the high boiling polar organic solvent and reflux conditions such as the degree of reduced pressure. However, the heating temperature is desirably set within a range of generally 210 to 350° C., preferably 220 to 300° C., more preferably 225 to 280° C. by controlling the reflux conditions.

The total reflux operation is desirably performed under conditions that the remaining rate of a melt phase of the glycolic acid oligomer is 0.5 or less, preferably 0.3 or less, more preferably zero (0). The remaining rate of the melt phase of the glycolic acid oligomer indicates a ratio of the volume of a melt phase of the glycolic acid oligomer, which is formed in the high boiling polar organic solvent actually used, to the volume (regarded as 1) of the glycolic acid oligomer, which is formed in a solvent substantially incapable of dissolving the glycolic acid oligomer, such as liquid paraffin.

In order to obtain high-purity glycolide, the total reflux operation is particularly preferably performed in a state that the remaining rate of the melt phase of the glycolic acid oligomer is substantially zero, and a homogeneous solution phase is formed. The homogeneous solution phase of the glycolic acid oligomer is formed in the mixture heated, whereby the effect by the total reflux operation can be enhanced. Thus, the solubilizing agent is preferably used.

The total reflux operation means that the total distillate distilled out during the reflux operation is cooled to return substantially the whole amount of the distillate to the original reflux system consisting of the mixture. Accordingly, distillates such as the high boiling polar organic solvent are not discharged into the outside of the reflux system during the total reflux operation. However, when the total reflux operation is performed under reduced pressure, a part of low-boiling matter such as water may be sucked by the vacuum device (vacuum pump) and discharged into the outside of the reflux system in some cases. The low-boiling matter discharged is captured by a cooled trap. Since the low-boiling matter such as water is an impurity, it is preferably removed. Accordingly, "substantially the whole amount of the distillate" in the present invention means that the case where a minor amount of other low-boiling matter than the high boiling polar organic solvent, glycolide and solubilizing agent is sucked by the vacuum device to be removed from the reflux system is also included.

The cooling temperature of the reflux condenser tube is controlled within a range of generally 70 to 150° C., preferably 75 to 120° C., more preferably 80 to 100° C. If the cooling temperature is too low, the removability of the low-boiling matter such as water is deteriorated. Since a part of the glycolic acid oligomer is presumed to be converted to glycolide under total reflux conditions, the glycolide distilled out is sucked by the vacuum device and discharged into the outside of the reflux system if the cooling temperature is too high.

The time of the total reflux operation is within a range of 0.1 to 20 hours, preferably 0.3 to 15 hours, more preferably 0.5 to 10 hours, particularly preferably 0.8 to 5 hours. If the time of the total reflux operation is too short, the effect by the total reflux operation becomes insufficient, and so it is difficult to obtain high-purity glycolide in the depolymerization reaction step. If the time of the total reflux operation is too long, the effect by the total reflux operation becomes a saturated state, and moreover thermal efficiency and productivity are lowered.

5. Depolymerization Reaction Step

In the depolymerization reaction step, the mixture after the total reflux operation or a mixture obtained by adding the high boiling polar organic solvent to a glycolic acid oligomer component recovered from the mixture after the total reflux operation is heated under normal or reduced pressure to a temperature at which the glycolic acid oligomer is depolymerized to depolymerize the glycolic acid oligomer in a solution phase, and moreover glycolide formed by the depolymerization is co-distillinged out of the depolymerization reaction system containing the mixture together with the high boiling polar organic solvent to the outside of the depolymerization reaction system.

In the depolymerization reaction step, the mixture after the total reflux operation may be used. The mixture after the total reflux operation may be used as it is. However, the high boiling polar organic solvent and solubilizing agent may be added if desired.

When the mixture after the total reflux operation is used in the depolymerization reaction step, the high boiling polar organic solvent and solubilizing agent accumulate in a reaction vessel unless the high boiling polar organic solvent is discharged into the outside of the depolymerization reaction system when the depolymerization reaction step is continuously performed (when the continuous operation is conducted) over a long period of time in the same reaction vessel (reaction tank), so that they overflow. In order to avoid the overflow, a method of discharging the high boiling polar organic solvent together with glycolide formed into the outside of the depolymerization reaction system during the continuous operation is adopted. When a solubilizing agent, which is substantially not distilled out during the continuous operation of the depolymerization reaction, is used, the solubilizing agent accumulates in the reaction vessel according to this method. In addition, the molar ratio of the glycolic acid oligomer to the solubilizing agent varies according to this method.

When the solubilizing agent had accumulated in the depolymerization reaction system, or there is need to keep the molar ratio of the glycolic acid oligomer to the solubilizing agent, a glycolic acid oligomer component is recovered from the mixture after the total reflux operation, and this component may be added into the depolymerization reaction system. The glycolic acid oligomer component after the total reflux operation is presumed to contain an unreacted glycolic acid oligomer and glycolide.

When a melt phase of the glycolic acid oligomer component is formed in the course of cooling the mixture after the total reflux operation, the melt phase is collected in a lower layer due to a difference in specific gravity, so that the melt phase can be easily separated from the high boiling polar organic solvent in an upper layer. The glycolic acid oligomer component may also be separated by a method of precipitating the glycolic acid oligomer component from the mixture after the total reflux operation and sieving the precipitate. Part of the high boiling polar organic solvent and solubilizing agent used in the total reflux operation may remain in the glycolic acid oligomer component recovered from the mixture after the total reflux operation.

The glycolic acid oligomer component recovered from the mixture after the total reflux operation is mixed with the high boiling polar organic solvent and optionally the solubilizing agent. During the continuous operation of the depolymerization reaction, a glycolic acid oligomer component (glycolic acid oligomer component after the total reflux operation) is continuously or intermittently added in an amount corresponding to the amount of glycolide taken out of the depolymerization reaction system into the depolymerization reaction system.

A quantitative ratio between the respective components in the depolymerization reaction step is substantially the same as that in the total reflux operation step. The high boiling polar organic solvent is used in a proportion of generally 0.3 to 50 times by mass, preferably 0.5 to 20 times by mass as much as the glycolic acid oligomer charged. When a part of the glycolic acid oligomer is converted to glycolide in the total reflux operation step, the quantitative ratio of the glycolic acid oligomer component to the high boiling polar organic solvent is calculated out on the basis of the amount of the glycolic acid oligomer charged in the total reflux step.

If the proportion of the high boiling polar organic solvent is too low, a proportion of the solution phase of the glycolic acid oligomer in the mixture containing the glycolic acid oligomer and the high boiling polar organic solvent is lowered under temperature conditions for the depolymerization of the glycolic acid oligomer (a proportion of the melt phase of the glycolic acid oligomer is increased) to lower the depolymerization reactivity of the glycolic acid oligomer. If the proportion of the high boiling polar organic solvent is too high, a thermal efficiency in the depolymerization reaction is lowered to lower productivity of glycolide by the depolymerization reaction.

When the solubilizing agent is used in the depolymerization reaction step, the solubilizing agent is used in a proportion of generally 0.1 to 500 parts by mass, preferably 1 to 300 parts by mass per 100 parts by mass of the glycolic acid oligomer charged. When the solubilizing agent is used in the depolymerization reaction step, the molar ratio (glycolic acid oligomer/solubilizing agent) of the glycolic acid oligomer charged to the solubilizing agent is controlled within a range of preferably 1 to 99, more preferably 3 to 70, still more preferably 5 to 50, whereby higher-purity glycolide can be obtained.

When the solubilizing agent accumulates in the depolymerization reaction system without being distilled out in the depolymerization reaction step, the molar ratio of the glycolic acid oligomer charged to the solubilizing agent is preferably set greater to control the molar ratio so as to fall within the above range even when the solubilizing agent accumulates due to the continuous operation. The molar ratio may not fall within the above range so far as the depolymerization reaction can be efficiently continued even when the solubilizing agent accumulates.

The heating temperature upon the depolymerization is not lower than a temperature at which depolymerization of the glycolic acid oligomer takes place, and is generally at least 200° C. though it varies according to the degree of reduced pressure, the kind of the high boiling polar organic solvent, etc. The heating temperature is within a range of generally 200 to 350° C., preferably 210 to 310° C., more preferably 220 to 300° C., particularly preferably 230 to 290° C.

As the high boiling polar organic solvent used in the depolymerization reaction step, is preferred an aromatic dicarboxylic acid diester, aromatic carboxylic acid ester, aliphatic dicarboxylic acid diester or polyalkylene glycol diether, and a polyalkylene glycol diether is more preferred in that it is hard to cause deterioration by heat. The polyalkylene glycol diether is preferably the compound represented by the above formula 1.

The solubilizing agent used in the depolymerization reaction is preferably at least one non-basic organic compound selected from the group consisting of monohydric alcohols, polyhydric alcohols, phenols, monovalent aliphatic carboxylic acids, polyvalent aliphatic carboxylic acids, aliphatic amides, aliphatic imides, polyalkylene glycol diethers having a molecular weight higher than 450 and sulfonic acids, said compounds each having a boiling point of 180° C. or higher. The solubilizing agent is preferably the polyalkylene glycol monoether represented by the above formula 2 or the polyalkylene glycol represented by the above formula 3.

The heating upon the depolymerization reaction is conducted under normal or reduced pressure and is preferably conducted under a reduced pressure of 0.1 to 90 kPa. As the pressure is lower, the temperature for the depolymerization reaction becomes lower, leading to a higher rate of the solvent recovery. The degree of reduced pressure is preferably 1 to 60 kPa, more preferably 1.5 to 40 kPa, particularly preferably 2 to 30 kPa.

By the heating, the depolymerization reaction of the glycolic acid oligomer is caused to proceed to distil out glycolide (boiling point under atmospheric pressure: 240 to 241° C.) together with the high boiling polar organic solvent. This is called co-distillation. If the high boiling polar organic solvent is not co-distilled out upon the distilling-out of the glycolide, the glycolide is liable to deposit on the inner wall of the line and attach thereto.

In the depolymerization reaction step, the mixture containing the glycolic acid oligomer, the high boiling polar organic solvent and optionally the solubilizing agent is heated to form a solution phase of the glycolic acid oligomer. The depolymerization reaction is desirably performed under conditions that the remaining rate of the melt phase of the glycolic acid oligomer is 0.5 or less, preferably 0.3 or less, more preferably zero. The depolymerization reaction is particularly preferably performed in a state that the remaining rate of the melt phase of the glycolic acid oligomer is substantially zero, and a homogeneous solution phase is formed for efficiently obtaining high-purity glycolide.

Since the depolymerization reaction is a reversible reaction, the depolymerization reaction of the glycolic acid oligomer is caused to efficiently proceed when the glycolide is distilled out of the liquid phase and discharged into the outside of the depolymerization reaction system. The high boiling polar organic solvent remaining in the depolymerization reaction system after the depolymerization reaction can be recovered by continuing the heating.

6. Collecting Step of Glycolide

The glycolide formed by the depolymerization in the depolymerization reaction step 2 is co-distilled out together with the high boiling polar organic solvent into the outside of the depolymerization reaction system, and the glycolide is collected from the co-distillate co-distilled out.

More specifically, the co-distillate is cooled and liquefied through a heat exchanger (condenser) to phase-separate the glycolide and the high boiling polar organic solvent in a liquid state. When the co-distillate is phase-separated, a glycolide phase (glycolide layer) is formed as a lower layer, and a high boiling polar organic solvent phase (layer containing the high boiling polar organic solvent) is formed as an upper layer. The glycolide in the lower layer can be separated and recovered as a liquid. In order to phase-separate the glycolide and the high boiling polar organic solvent in the liquid state, the cooling temperature is controlled within a range of generally 70 to 180° C., preferably 75 to 150° C., more preferably 80 to 120° C. If the cooling temperature is too high, side reactions such as a ring-opening reaction are liable to occur in the glycolide phase during the separating and recovering operations. If the cooling temperature is too low, it is difficult to phase-separate them in the liquid state.

When the depolymerization reaction is continued while controlling the temperature of the co-distillate by the heat exchanger, the glycolide co-distilled out together with the high boiling polar organic solvent passes through the upper solvent phase of the co-distillate in the form of droplets and is condensed into the lower glycolide phase.

The high boiling polar organic solvent left after removal of the glycolide from the co-distillate may be discharged into the outside of the depolymerization reaction system and reused. The high boiling polar organic solvent may also be purified by being adsorbed on active carbon or by distillation before reuse. When the polyalkylene glycol diether, which is excellent in heat stability, is used as the high boiling polar organic solvent, almost the whole amount of the high boiling polar organic solvent recovered from the co-distillate may be reused without purification.

In the present invention, the co-distillate may be phase-separated as it is in the liquid state to separate and recover the glycolide from the glycolide phase (glycolide layer; lower layer), and the phase (upper layer) containing the high boiling polar organic solvent may be recycled into the depolymerization reaction system. The phase (upper layer) containing the high boiling polar organic solvent may be taken out and reused as it is or after purifying it. More specifically, the co-distillate is stored in a separation vessel to conduct phase separation. The separation vessel is temperature-controlled to a temperature, at which the co-distillate is kept liquid, with a heat medium such as hot water. When the co-distillate is phase-separated, a glycolide phase is collected in a lower layer, and a solvent phase is collected in an upper layer. In order to phase-separate the glycolide and the solvent in the liquid state, the temperature of the separation vessel is controlled within a range of generally 70 to 180° C., preferably 75 to 150° C., more preferably 80 to 120° C.

The glycolide separated is purified by recrystallization, washing and/or the like as needed. According to this method, it is not necessary to separate a great amount of the solvent from the glycolide recovered, and a separating operation between the solvent and the glycolide is simplified. On the other hand, almost the whole amount of the mother liquor (a distillate fraction containing the high boiling polar organic solvent) obtained by removing the glycolide may be reused without subjecting it to a step such as purification. The distillate fraction containing the high boiling polar organic solvent may also be purified by being adsorbed on active carbon or by distillation before reuse.

Figure 2:
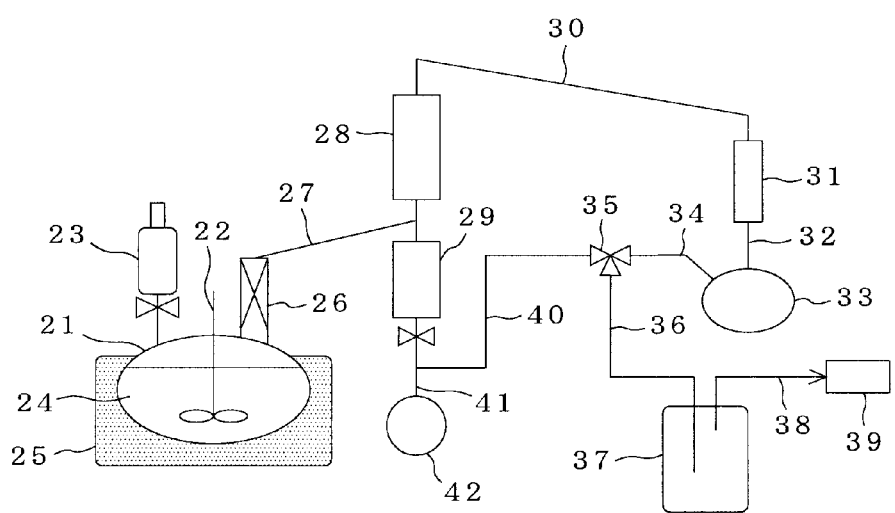
FIG. 2 is an explanatory view illustrating an exemplary apparatus for conducting a depolymerization reaction.

The depolymerization reaction step and the collecting step of glycolide can be performed by means of, for example, an apparatus illustrated in FIG. 2. FIG. 2 schematically illustrates an exemplary apparatus for performing a depolymerization reaction. A stirring device 22 equipped with a stiffing blade is arranged in a reaction vessel (reaction tank) 21, and the mixture after the total reflux operation or a glycolic acid oligomer component recovered from the mixture after the total reflux operation is poured into the reaction vessel 21 from a raw material input port 23. When the glycolic acid oligomer component recovered from the mixture after the total reflux operation is poured, the high boiling polar organic solvent and optionally the solubilizing agent are also poured.

In such a manner, a depolymerization reaction system comprising a mixture 24 is formed. A heating means 25 such as a mantle heater is arranged in the exterior of the reaction vessel 21 to heat the mixture 24, thereby dissolving the glycolic acid oligomer to form a solution phase thereof. When the heating is continued, a distillate containing the glycolide and high boiling polar organic solvent is distilled out of the depolymerization reaction system and reaches a first heat exchanger 28 through a piping 27 from a distillation column 26, and the distillate (co-distillate) cooled therein is stored in a separation vessel 29. The distillation column 26 fulfills the role of controlling the temperature of the distillate in such a manner that the distillate smoothly reaches the first heat exchanger tube 28 from the piping 27. The temperature of the first heat exchanger 28 is controlled within a range of generally 70 to 180° C., preferably 75 to 150° C., more preferably 80 to 120° C.

A distillate passed through the first heat exchanger 28 is cooled in a second heat exchanger 31 through a piping 30 and trapped in a first cooling trap (for example, an ice bath trap) 33 through a piping 32. The temperature of the second heat exchanger 31 is controlled within a range of generally 15 to 70° C., preferably 20 to 30° C.

In order to conduct the depolymerization reaction under reduced pressure, a piping 38 is connected to a vacuum device (for example, a vacuum pump) 39. The first cooling trap 33 is connected to a second cooling trap 37 (for example, a dry ice trap) through a piping 34, a valve 35 and a piping 36 to trap low-boiling matter not trapped in the first cooling trap 33 is trapped in the second cooling trap 37.

The glycolide in the lower layer, which has been phase-separated in the separation vessel 29, is taken out in a container 42 through a piping 41. An upper layer in the separation vessel 29 is taken out after the depolymerization reaction, or taken out from a discharge port (not illustrated) provided in the separation vessel.

7. Continuous Operation

In the production process according to the present invention, the above-described Steps 1 to 3 can be performed by a continuous operation according to a process of combining the following respective steps:

a) Step a of continuously or intermittently feeding the mixture after the total reflux operation or the glycolic acid oligomer component recovered from the mixture after the total reflux operation, which has been prepared in Step 1, into the depolymerization reaction system;

b) Step b of heating the mixture after the total reflux operation or a mixture obtained by adding the high boiling polar organic solvent to the glycolic acid oligomer component recovered from the mixture after the total reflux operation under normal or reduced pressure to a temperature at which the glycolic acid oligomer is depolymerized to continuously depolymerize the glycolic acid oligomer in a solution phase in Step 2, and moreover continuously co-distilling glycolide formed by the depolymerization out of the depolymerization reaction system containing the mixture together with the high boiling polar organic solvent into the outside of the depolymerization reaction system; and (c) Step c of continuously or intermittently collecting glycolide from a lower layer of the co-distillate cooled into a liquid state by utilizing a difference in specific gravity between a distillate fraction containing the high boiling polar organic solvent and the glycolide in Step 3.

In Step c, the glycolide may be continuously or intermittently collected from the lower layer of the co-distillate cooled into the liquid state, and the distillate fraction containing the high boiling polar organic solvent in an upper layer of the co-distillate may be continuously or intermittently discharged.

In Step c, the glycolide may be continuously or intermittently collected from the lower layer of the co-distillate cooled into the liquid state, and the distillate fraction containing the high boiling polar organic solvent in the upper layer of the co-distillate may be continuously or intermittently returned into the depolymerization reaction system.

Figure 3:
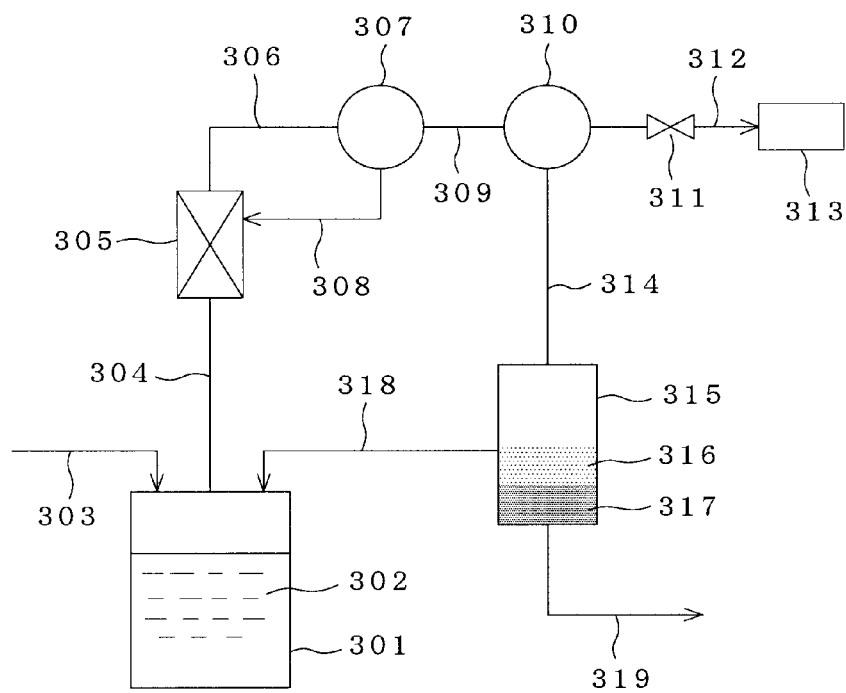
FIG. 3 is an explanatory view illustrating an exemplary apparatus used in a continuous operation of a depolymerization reaction.

FIG. 3 illustrates an exemplary depolymerization reaction apparatus for performing a continuous operation. FIG. 3 illustrates principal parts of the depolymerization reaction apparatus, and detailed portions of a stirring device, a heating device, traps, valves, etc. are omitted.

A depolymerization reaction tank (reaction vessel) 301 is charged with the mixture 302 after the total reflux operation or a mixture 302 obtained by adding the high boiling polar organic solvent to the glycolic acid oligomer component recovered from the mixture after the total reflux operation. The mixture 302 may be caused to contain the solubilizing agent if desired.

While stirring the mixture 302, the reaction tank 301 is heated under normal or reduced pressure to depolymerize the glycolic acid oligomer in a solution phase, and glycolide formed by the depolymerization is distilled (co-distilled) out of the depolymerization reaction system containing the mixture together with the high boiling polar organic solvent. The respective distillates reach a first heat exchanger 307 through a piping 304, a distillation column 305 and a piping 306, and cooled to a temperature within a range of generally 70 to 180° C., preferably 75 to 150° C., more preferably 80 to 120° C. in the first heat exchanger 307. Part of the cooled distillates may be returned to the distillation column 305 by connecting the first heat exchanger 307 to the distillation column 305 through a piping 308. The respective distillates passed through the first heat exchanger 307 are cooled in a second heat exchanger 310. The co-distillate cooled into a liquid state is stored in a separation vessel 315 through a piping 314. When the depolymerization reaction is performed under reduced pressure, the depolymerization reaction system is connected to a vacuum device 313 through a valve 311 and a piping 312.

The co-distillate in the liquid state is phase-separated (layer-separated) into an upper layer 316 consisting of a distillate fraction containing the high boiling polar organic solvent and a lower layer 317 consisting of a glycolide phase in the separation vessel 315. The glycolide in the lower layer 317 is continuously or intermittently recovered through a piping 319. On the other hand, the distillate fraction in the upper layer 316 is continuously or intermittently returned into the depolymerization reaction system through a piping 318. The distillate fraction in the upper layer 316 may be continuously or intermittently discharged into the outside of the system instead of being returned into the depolymerization reaction system to reuse it.

With the distilling-out of the glycolide and the recovery thereof into the outside of the system, the amount of the mixture 302 in the depolymerization reaction system is reduced, and so the mixture after the total reflux operation or the glycolic acid oligomer component recovered from the mixture after the total reflux operation is continuously or intermittently additionally poured into the depolymerization reaction system from a raw material input line 303. When the amount of the high boiling polar organic solvent discharged into the outside of the system is great, the high boiling polar organic solvent may also be additionally poured. In this manner, the depolymerization reaction can be performed by the continuous operation.

8. Glycolide

The purity of the glycolide (also referred to as crude glycolide) obtained by the production process according to the present invention is as high as preferably at least 99.0%, more preferably at least 99.3%, still more preferably at least 99.5% from an initial stage of the depolymerization reaction. Therefore, high-purity glycolide can be obtained even when the depolymerization reaction is performed by a continuous operation while continuously or intermittently additionally pouring the mixture after the total reflux operation or the glycolic acid oligomer component recovered from the mixture after the total reflux operation.

According to the production process of the present invention, high-purity glycolide can be obtained even when a glycolic acid oligomer synthesized by using glycolic acid of an industrial grade is used as a starting material.

EXAMPLES

The present invention will hereinafter be described more specifically by the following Reference Examples, Comparative Examples and Examples. Measuring methods are as follows.

(1) Melting Point of Glycolic Acid Oligomer

The melting point of a glycolic acid oligomer is a value detected at the time the oligomer is heated at a rate of 10° C./min in an inert gas atmosphere by means of a differential scanning calorimeter (DSC).

(2) Purity of Glycolide

The purity of glycolide is a value determined by using 4-chlorobenzophenone as an internal standard by gas chromatography (GC).

Reference Example 1

Synthesis of Glycolic Acid Oligomer

A 1-liter separable flask was charged with 1 kg of a 70% aqueous solution (product of Du Pont Co.) of glycolic acid of an industrial grade. While stiffing under normal pressure, the contents were heated from room temperature to 220° C. over 4 hours to conduct a polycondensation reaction while distilling out water formed. The pressures inside the separable flask was then slowly reduced from normal pressure to 2 kPa over 1 hour, and the polycondensation reaction was continued additionally for 3 hours, thereby distilling off low-boiling matter such as an unreacted raw material and synthesizing 480 g of a glycolic acid oligomer. The melting point of this glycolic acid oligomer was 211° C.

Comparative Example 1

The apparatus illustrated in FIG. 2 was used, a 500-ml flask was charged with 160 g of the glycolic acid oligomer obtained in Reference Example 1, 100 g of tetraethylene glycol dibutyl ether and 89 g of triethylene glycol monooctyl ether as a solubilizing agent, and the contents were then heated to 230° C. to form a uniform solution in the reaction system. While heating this solution at a temperature of 230° C., tetraethylene glycol dibutyl ether and glycolide formed were co-distilled out under a reduced pressure of 4.5 kPa. After the depolymerization reaction was continued for 1 hour, 13 g of glycolide was collected from the co-distillate. The purity of this glycolide was analyzed and found to be 93.4%.

When the depolymerization reaction was conducted additionally for 1 hour, the purity of glycolide obtained from a co-distillate during this 1 hour was raised to 97.0%.

Example 1

The apparatus illustrated in FIG. 1 was used, a 500-ml flask was charged with 160 g of the glycolic acid oligomer obtained in Reference Example 1, 100 g of tetraethylene glycol dibutyl ether and 89 g of triethylene glycol monooctyl ether as a solubilizing agent, and the contents were then heated to 230° C. to form a uniform solution in the reaction system. While heating this solution at a temperature of 230° C., a total reflux operation was conducted for 3 hours under a reduced pressure of 4.5 kPa.

The apparatus illustrated in FIG. 2 was used to heat the mixture after the total reflux operation to 230° C., thereby forming a uniform solution in the reaction system. While heating this solution at a temperature of 230° C., tetraethylene glycol dibutyl ether and glycolide formed were co-distilled out under a reduced pressure of 4.5 kPa. A depolymerization reaction was conducted for 1 hour. As a result, 9.3 g of glycolide was obtained. The purity of this glycolide was analyzed and found to be 99.6%.

When the depolymerization reaction was conducted additionally for 1 hour, the purity of glycolide obtained from a co-distillate during this 1 hour was raised to 100.0%.
<Consideration>

As apparent from the comparison results between Comparative Example 1 and Example 1, high-purity glycolide can be obtained from an initial stage of the depolymerization reaction according to the production process of the present invention. Therefore, according to the production process of the present invention, the high-purity glycolide can be obtained even when the depolymerization reaction is performed by a continuous operation while continuously or intermittently additionally pouring the mixture after the total reflux operation or the glycolic acid oligomer component recovered from the mixture after the total reflux operation.

Comparative Example 2

The apparatus illustrated in FIG. 2 was used, a 500-ml flask was charged with 160 g of the glycolic acid oligomer obtained in Reference Example 1, 100 g of diethylene glycol butyl 2-chlorophenyl ether and 95 g of diethylene glycol monodecyl ether as a solubilizing agent, and the contents were then heated to 225° C. to form a uniform solution in the reaction system. While heating this solution at a temperature of 225° C., diethylene glycol butyl 2-chlorophenyl ether and glycolide formed were co-distilled out under a reduced pressure of 4.0 kPa. After the depolymerization reaction was continued for 1 hour, 10.1 g of glycolide was collected from the co-distillate. The purity of this glycolide was analyzed and found to be 89.0%.

When the depolymerization reaction was conducted additionally for 1 hour, the purity of glycolide obtained from a co-distillate during this 1 hour was raised to 93.1%.

Example 2

The apparatus illustrated in FIG. 1 was used, a 500-ml flask was charged with 160 g of the glycolic acid oligomer obtained in Reference Example 1, 100 g of diethylene glycol butyl 2-chlorophenyl ether and 95 g of diethylene glycol monodecyl ether as a solubilizing agent, and the contents were then heated to 225° C. to form a uniform solution in the reaction system. While heating this solution at a temperature of 225° C., a total reflux operation was conducted for 1 hour under a reduced pressure of 4.0 kPa.

The apparatus illustrated in FIG. 2 was used to heat the mixture after the total reflux operation to 230° C., thereby forming a uniform solution in the reaction system. While heating this solution at a temperature of 225° C., diethylene glycol butyl 2-chlorophenyl ether and glycolide formed were co-distilled out under a reduced pressure of 4.0 kPa. A depolymerization reaction was conducted for 1 hour. As a result, 10.9 g of glycolide was obtained. The purity of this glycolide was analyzed and found to be 94.6%.

When the depolymerization reaction was conducted additionally for 1 hour, the purity of glycolide obtained from a co-distillate during this 1 hour was raised to 99.0%.
<Consideration>

As apparent from the comparison results between Comparative Example 2 and Example 2, high-purity glycolide can be obtained from an initial stage of the depolymerization reaction according to the production process of the present invention.

Comparative Example 3

The apparatus illustrated in FIG. 2 was used, a 500-ml flask was charged with 160 g of the glycolic acid oligomer obtained in Reference Example 1, 100 g of diethylene glycol dibutyl ether and 84 g of diethylene glycol monohexyl ether as a solubilizing agent, and the contents were then heated to 220° C. to form a uniform solution in the reaction system. While heating this solution at a temperature of 220° C., diethylene glycol dibutyl ether and glycolide formed were co-distilled out under a reduced pressure of 5.5 kPa. After the depolymerization reaction was continued for 1 hour, 8.8 g of glycolide was collected from the co-distillate. The purity of this glycolide was analyzed and found to be 88.2%.

When the depolymerization reaction was conducted additionally for 1 hour, the purity of glycolide obtained from a co-distillate during this 1 hour was raised to 91.5%.

Example 3

The apparatus illustrated in FIG. 1 was used, a 500-ml flask was charged with 160 g of the glycolic acid oligomer obtained in Reference Example 1, 100 g of diethylene glycol dibutyl ether and 84 g of diethylene glycol monodecyl ether as a solubilizing agent, and the contents were then heated to 220° C. to form a uniform solution in the reaction system. While heating this solution at a temperature of 225° C., a total reflux operation was conducted for 5 hours under a reduced pressure of 5.5 kPa.

The apparatus illustrated in FIG. 2 was used to heat the mixture after the total reflux operation to 220° C., thereby forming a uniform solution in the reaction system. While heating this solution at a temperature of 225° C., diethylene glycol dibutyl ether and glycolide formed were co-distilled out under a reduced pressure of 5.5 kPa. A depolymerization reaction was conducted for 1 hour. As a result, 9.2 g of glycolide was obtained. The purity of this glycolide was analyzed and found to be 99.0%.

When the depolymerization reaction was conducted additionally for 1 hour, the purity of glycolide obtained from a co-distillate during this 1 hour was raised to 99.6%.
<Consideration>

As apparent from the comparison results between Comparative Example 3 and Example 3, high-purity glycolide can be obtained from an initial stage of the depolymerization reaction according to the production process of the present invention.

Comparative Example 4

The apparatus illustrated in FIG. 2 was used, a 500-ml flask was charged with 160 g of the glycolic acid oligomer obtained in Reference Example 1, 100 g of triethylene glycol butyl decyl ether and 100 g of polyethylene glycol monomethyl ether as a solubilizing agent, and the contents were then heated to 220° C. to form a uniform solution in the reaction system. While heating this solution at a temperature of 235° C., triethylene glycol butyl decyl ether and glycolide formed were co-distilled out under a reduced pressure of 2.5 kPa. After the depolymerization reaction was continued for 1 hour, 9.8 g of glycolide was collected from the co-distillate. The purity of this glycolide was analyzed and found to be 90.2%.

When the depolymerization reaction was conducted additionally for 1 hour, the purity of glycolide obtained from a co-distillate during this 1 hour was raised to 94.5%.

Example 4

The apparatus illustrated in FIG. 1 was used, a 500-ml flask was charged with 160 g of the glycolic acid oligomer obtained in Reference Example 1, 100 g of triethylene glycol butyl decyl ether and 100 g of polyethylene glycol monomethyl ether as a solubilizing agent, and the contents were then heated to 235° C. to form a uniform solution in the reaction system. While heating this solution at a temperature of 225° C., a total reflux operation was conducted for 2 hours under a reduced pressure of 2.5 kPa.

The apparatus illustrated in FIG. 2 was used to heat the mixture after the total reflux operation to 220° C., thereby forming a uniform solution in the reaction system. While heating this solution at a temperature of 225° C., triethylene glycol butyl decyl ether and glycolide formed were co-distilled out under a reduced pressure of 5.5 kPa. A depolymerization reaction was conducted for 1 hour. As a result, 10.5 g of glycolide was obtained. The purity of this glycolide was analyzed and found to be 99.1%.

When the depolymerization reaction was conducted additionally for 1 hour, the purity of glycolide obtained from a co-distillate during this 1 hour was raised to 99.7%.
<Consideration>

As apparent from the comparison results between Comparative Example 4 and Example 4, high-purity glycolide can be obtained from an initial stage of the depolymerization reaction according to the production process of the present invention.

Comparative Example 5

The apparatus illustrated in FIG. 2 was used, a 500-ml flask was charged with 160 g of the glycolic acid oligomer obtained in Reference Example 1, 100 g of triethylene glycol butyl hexyl ether and 100 g of polyethylene glycol monohexyl ether as a solubilizing agent, and the contents were then heated to 220° C. to form a uniform solution in the reaction system. While heating this solution at a temperature of 220° C., triethylene glycol butyl hexyl ether and glycolide formed were co-distilled out under a reduced pressure of 3.5 kPa. After the depolymerization reaction was continued for 1 hour, 10.8 g of glycolide was collected from the co-distillate. The purity of this glycolide was analyzed and found to be 92.2%.

When the depolymerization reaction was conducted additionally for 1 hour, the purity of glycolide obtained from a co-distillate during this 1 hour was raised to 96.8%.

Example 5

The apparatus illustrated in FIG. 1 was used, a 500-ml flask was charged with 160 g of the glycolic acid oligomer obtained in Reference Example 1, 100 g of triethylene glycol butyl hexyl ether and 100 g of polyethylene glycol monohexyl ether as a solubilizing agent, and the contents were then heated to 235° C. to form a uniform solution in the reaction system. While heating this solution at a temperature of 220° C., a total reflux operation was conducted for 2 hours under a reduced pressure of 3.5 kPa.

The apparatus illustrated in FIG. 2 was used to heat the mixture after the total reflux operation to 220° C., thereby forming a uniform solution in the reaction system. While heating this solution at a temperature of 225° C., triethylene glycol butyl hexyl ether and glycolide formed were co-distilled out under a reduced pressure of 3.5 kPa. A depolymerization reaction was conducted for 1 hour. As a result, 11.5 g of glycolide was obtained. The purity of this glycolide was analyzed and found to be 99.3%.

When the depolymerization reaction was conducted additionally for 1 hour, the purity of glycolide obtained from a co-distillate during this 1 hour was raised to 100%.
<Consideration>

As apparent from the comparison results between Comparative Example 5 and Example 5, high-purity glycolide can be obtained from an initial stage of the depolymerization reaction according to the production process of the present invention.

Comparative Example 6

The apparatus illustrated in FIG. 2 was used, a 500-ml flask was charged with 160 g of the glycolic acid oligomer obtained in Reference Example 1 and 100 g of tetraethylene glycol dibutyl ether, and the contents were then heated to 230° C. to form a uniform solution in the reaction system. While heating this solution at a temperature of 230° C., tetraethylene glycol dibutyl ether and glycolide formed were co-distilled out under a reduced pressure of 5.5 kPa. After the depolymerization reaction was continued for 1 hour, 9.8 g of glycolide was collected from the co-distillate. The purity of this glycolide was analyzed and found to be 93.1%.

When the depolymerization reaction was conducted additionally for 1 hour, the purity of glycolide obtained from a co-distillate during this 1 hour was raised to 96.0%.

Example 6

The apparatus illustrated in FIG. 1 was used, a 500-ml flask was charged with 160 g of the glycolic acid oligomer obtained in Reference Example 1 and 100 g of tetraethylene glycol dibutyl ether, and the contents were then heated to 230° C. to form a uniform solution in the reaction system. While heating this solution at a temperature of 230° C., a total reflux operation was conducted for 3 hours under a reduced pressure of 5.5 kPa.

The apparatus illustrated in FIG. 2 was used to heat the mixture after the total reflux operation to 230° C., thereby forming a uniform solution in the reaction system. While heating this solution at a temperature of 230° C., tetraethylene glycol dibutyl ether and glycolide formed were co-distilled out under a reduced pressure of 5.5 kPa. A depolymerization reaction was conducted for 1 hour. As a result, 11.0 g of glycolide was obtained. The purity of this glycolide was analyzed and found to be 96.3%.

When the depolymerization reaction was conducted additionally for 1 hour, the purity of glycolide obtained from a co-distillate during this 1 hour was raised to 98.0%.

<Consideration>

As apparent from the comparison results between Comparative Example 6 and Example 6, high-purity glycolide can be obtained from an initial stage of the depolymerization reaction according to the production process of the present invention.

INDUSTRIAL APPLICABILITY

According to the production process of the present invention, high-purity glycolide can be obtained from an initial stage of the depolymerization reaction. Therefore, according to the production process of the present invention, high-purity glycolide can be obtained even when the depolymerization reaction is performed by a continuous operation while continuously or intermittently additionally pouring the mixture after the total reflux operation or the glycolic acid oligomer component recovered from the mixture after the total reflux operation.

The production process according to the present invention can be utilized for producing high-purity glycolide. The glycolide obtained by the production process according to the present invention can be utilized for producing polyglycolic acid.

DESCRIPTION OF CHARACTERS

1 Reaction vessel
5 Heating means
8 Reflux condenser tube
10 First cooling trap
14 Second cooling trap
16 Vacuum device
21 Reaction vessel
25 Heating means
28 First heat exchanger
29 Separation vessel
31 Second heat exchanger
33 First cooling trap
37 Second cooling trap
39 Vacuum device
42 Container
301 Reaction tank
302 Mixture
303 Raw material input line
305 Distillation column
307 First heat exchanger
310 Second heat exchanger
313 Vacuum device
315 Separation vessel
316 Solvent phase (upper layer)
317 Glycolide phase (lower layer)
318 Piping for returning solvent
319 Piping for recovering glycolide

The invention claimed is:

1. A production process of glycolide comprising a step of heating a mixture containing a glycolic acid oligomer and a high boiling polar organic solvent, thereby depolymerizing the glycolic acid oligomer in a solution phase, the process comprising the respective steps of:
   (1) Step 1 of heating the mixture containing the glycolic acid oligomer and the high boiling polar organic solvent having a boiling point within a range of 230 to 450° C. under reduced pressure to reflux the mixture and at that time, conducting a total reflux operation in a reflux time within a range of 0.5 to 15 hours, at a reduced pressure of 2.0 to 10 kPa and a heating temperature within a range of 220 to 280° C. under conditions wherein substantially the whole amount of a distillate distilled out of a reflux system containing the mixture is refluxed into the reflux system and a part of low-boiling matter comprising water is discharged outside of the reflux system;
   (2) Step 2 of heating (i) the mixture after the total reflux operation, or (ii) or a mixture obtained by adding the high boiling polar organic solvent to a glycolic acid oligomer component recovered from the mixture after the total reflux operation, under normal or reduced pressure to a temperature at which the glycolic acid oligomer is depolymerized to depolymerize the glycolic acid oligomer in a solution phase, and moreover co-distilling glycolide formed by the depolymerization out of the depolymerization reaction system containing the mixture together with the high boiling polar organic solvent outside of the depolymerization reaction system; and
   (3) Step 3 of collecting glycolide from the co-distillate, the co-distillate being cooled and liquefied to phase-separate the glycolide and the high boiling polar organic solvent in a liquid state,
wherein
   (a) the mixture used in Step 1 further comprises, in addition to the glycolic acid oligomer and the high boiling polar organic solvent, a solubilizing agent comprising at least one non-basic organic compound selected from the group consisting of monohydric alcohols, polyhydric alcohols, phenols, monovalent aliphatic carboxylic acids, polyvalent aliphatic carboxylic acids, aliphatic amides, aliphatic imides, polyalkylene glycol diethers having a molecular weight higher than 450, and sulfonic acids, said compounds each having a boiling point of 180° C. or higher, and the mixture used in Step 1 comprises a molar ratio of the glycolic acid oligomer to the solubilizing agent within a range of 1 to 99, (b) the high boiling polar organic solvent used in Step 1 or Step 2 has a molecular weight within a range of 150 to 450 and comprises a solvent selected from the group consisting of aromatic dicarboxylic acid diesters, aromatic carboxylic acid esters, aliphatic dicarboxylic acid diesters, polyalkylene glycol diethers, aromatic dicarboxylic acid dialkoxyalkyl esters, aliphatic dicarboxylic acid dialkoxyalkyl esters, polyalkylene glycol diesters and aromatic phosphoric acid esters, and (c) in Step 1, a mass ratio of the high boiling polar organic solvent to the glycolic acid oligomer is within a range of 0.3 to 50.

2. The production process according to claim 1, wherein the glycolic acid oligomer is a low-molecular weight polyglycolic acid having a weight-average molecular weight of 20,000 or lower.

3. The production process according to claim 1, wherein the high boiling polar organic solvent is a polyalkylene glycol diether represented by the following formula 1:

$$X^1 \text{—} O \text{—} (R^1 \text{—} O)_p \text{—} Y \quad (1)$$

wherein $R^1$ is a methylene group, or a linear or branched alkylene group having 2 to 8 carbon atoms, $X^1$ is a hydrocarbon group, Y is an alkyl group having 2 to 20 carbon atoms or an aryl group, and p is an integer of 1 or greater, with the proviso that when p is 2 or greater, plural $R^1$ groups may be the same or different from each other, and having a molecular weight of 150 to 450.

4. The production process according to claim 1, wherein the solubilizing agent comprises a monohydric alcohol selected from polyalkylene glycol monoethers represented by the following formula 2:

$$OH \text{—} (R^2 \text{—} O)_q \text{—} X^2 \quad (2)$$

wherein $R^2$ is a methylene group, or a linear or branched alkylene group having 2 to 8 carbon atoms, $X^2$ is a hydrocarbon group, and q is an integer of 1 or greater, with the proviso that when q is 2 or greater, plural $R^2$ groups may be the same or different from each other, and having a boiling point of 250° C. or higher.

5. The production process according to claim 1, wherein the solubilizing agent comprises a polyhydric alcohol selected from polyalkylene glycols represented by the following formula 3:

$$OH \text{—} (R^3 \text{—} O)_r \text{—} H \quad (3)$$

wherein $R^3$ is a methylene group, or a linear or branched alkylene group having 2 to 8 carbon atoms, and r is an integer of 1 or greater, with the proviso that when r is 2 or greater, plural $R^3$ groups may be the same or different from each other, and having a boiling point of 250° C. or higher.

6. The production process according to claim 1, wherein when a mixture obtained by adding the high boiling polar organic solvent to a glycolic acid oligomer component recovered from the mixture after the total reflux operation is used in Step 2, the mixture is a mixture further containing, as a solubilizing agent, at least one non-basic organic compound selected from the group consisting of monohydric alcohols, polyhydric alcohols, phenols, monovalent aliphatic carboxylic acids, polyvalent aliphatic carboxylic acids, aliphatic amides, aliphatic imides, polyalkylene glycol diethers having a molecular weight higher than 450 and sulfonic acids, said compounds each having a boiling point of 180° C. or higher.

7. The production process according to claim 6, wherein the solubilizing agent in Step (2) comprises a monohydric alcohol selected from polyalkylene glycol monoethers represented by the following formula 2:

$$OH \text{—} (R^2 \text{—} O)_q \text{—} X^2 \quad (2)$$

wherein $R^2$ is a methylene group, or a linear or branched alkylene group having 2 to 8 carbon atoms, $X^2$ is a hydrocarbon group, and q is an integer of 1 or greater, with the proviso that when q is 2 or greater, plural $R^2$ groups may be the same or different from each other, and having a boiling point of 250° C. or higher.

8. The production process according to claim 6, wherein the solubilizing agent in Step (2) comprises a polyhydric alcohol selected from polyalkylene glycols represented by the following formula 3:

$$OH \text{—} (R^3 \text{—} O)_r \text{—} H \quad (3)$$

wherein $R^3$ is a methylene group, or a linear or branched alkylene group having 2 to 8 carbon atoms, and r is an integer of 1 or greater, with the proviso that when r is 2 or greater, plural $R^3$ groups may be the same or different from each other, and having a boiling point of 250° C. or higher.

9. The production process according to claim 6, wherein when a mixture obtained by adding the high boiling polar organic solvent to a glycolic acid oligomer component recovered from the mixture after the total reflux operation is used in Step 2, the mixture is a mixture containing the solubilizing agent in a proportion that the molar ratio of the glycolic acid oligomer to the solubilizing agent falls within a range of 1 to 99.

10. The production process according to claim 1, wherein the above-described Steps 1 to 3 are performed by a continuous operation according to a process of combining the following respective steps:

a) Step a of continuously or intermittently feeding the mixture after the total reflux operation or the glycolic acid oligomer component recovered from the mixture after the total reflux operation, which has been prepared in Step 1, into the depolymerization reaction system;

b) Step b of heating the mixture after the total reflux operation or a mixture obtained by adding the high boiling polar organic solvent to the glycolic acid oligomer component recovered from the mixture after the total reflux operation under normal or reduced pressure to a temperature at which the glycolic acid oligomer is depolymerized to continuously depolymerize the glycolic acid oligomer in a solution phase in Step 2, and moreover continuously co-distilling glycolide formed by the depolymerization out of the depolymerization reaction system containing the mixture together with the high boiling polar organic solvent into the outside of the depolymerization reaction system; and (c) Step c of continuously or intermittently collecting the glycolide from a lower layer of the co-distillate cooled into a liquid state by utilizing a difference in specific gravity between a distillate fraction containing the high boiling polar organic solvent and the glycolide in Step 3.

11. The production process according to claim 10, wherein in Step c, the glycolide is continuously or intermittently collected from the lower layer of the co-distillate cooled into the liquid state, and the distillate fraction containing the high boiling polar organic solvent in an upper layer of the co-distillate is continuously or intermittently discharged.

12. The production process according to claim 10, wherein in Step c, the glycolide is continuously or intermittently collected from the lower layer of the co-distillate cooled into the liquid state, and the distillate fraction containing the high boiling polar organic solvent in the upper layer of the co-distillate is continuously or intermittently returned into the depolymerization reaction system.

13. The production process according to claim 1, wherein the glycolide collected from the co-distillate has a purity of at least 99.0%.

14. The production process according to claim 1, wherein the glycolide collected from the co-distillate has a purity of at least 99.5%.

* * * * *